United States Patent [19]

Jaeggi

[11] Patent Number: 4,929,606
[45] Date of Patent: May 29, 1990

[54] AZACYCLOALKYLALKANEDIPHOSPHONIC ACIDS USEFUL FOR TREATING DISEASES ATTRIBUTED TO CALCIUM METABOLISM DISORDERS

[75] Inventor: Knut A. Jaeggi, Basel, Switzerland

[73] Assignee: Ciba-Geigy Corporation, Ardsley, N.Y.

[21] Appl. No.: 267,585

[22] Filed: Nov. 7, 1988

[30] Foreign Application Priority Data

Nov. 13, 1987 [CH] Switzerland .................. 4435/87

[51] Int. Cl.$^5$ .................. C07F 9/65; A61K 31/675
[52] U.S. Cl. .................................. 514/80; 546/23
[58] Field of Search .................. 546/23; 514/80

[56] References Cited

U.S. PATENT DOCUMENTS

| 3,733,270 | 5/1973 | Kerst | 210/698 |
| 4,503,049 | 3/1985 | Biere et al. | 514/80 |
| 4,687,767 | 8/1987 | Bosies et al. | 514/89 |

FOREIGN PATENT DOCUMENTS

| 186405 | 7/1986 | European Pat. Off. | 514/89 |
| 0252504 | 1/1988 | European Pat. Off. | 260/502.4 P |
| 258618 | 3/1988 | European Pat. Off. | 548/112 |
| 3232997 | of 1984 | Fed. Rep. of Germany | 544/84 |
| 3623397 | 1/1988 | Fed. Rep. of Germany | 260/502.4 P |
| 5589293 | of 1978 | Japan | 544/84 |
| 54135724 | of 1978 | Japan | 548/112 |
| 1002300 | of 1983 | U.S.S.R. | 544/84 |

OTHER PUBLICATIONS

Alder et al., Helvetica Chimica Acta, vol. 65, pp. 2405–2412, (1982).
Alder et al., J. Am. Chem. Soc., vol. 105, pp. 6712–6714, (1983).
CA 92:146905v of Japanese 79, 135,724.
Derwent Abstr. 93:181017z of Japanese 80, 89,293.
Chem. Abst. 99:22702b, of SU 1,002,300, (1983).

*Primary Examiner*—Alan L. Rotman
*Attorney, Agent, or Firm*—JoAnn Villamizer

[57] ABSTRACT

Azacycloalkylalkanediphosphonic acids of formula

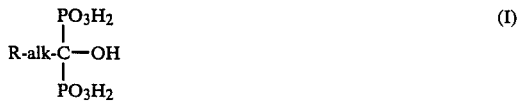
(I)

wherein R is an azabicycloalkyl radical that is attached by way of the aza ring member and is composed of ring systems each containing from 3 up to and including 8 members, and alk is lower alkylene, and their salts, have regulatory properties with regard to the calcium metabolism and can be used as medicaments for the treatment of diseases that can be attributed to calcium metabolism disorders. They are prepared, for example, by:

in a compound of formula

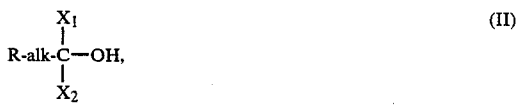
(II)

wherein $X_1$ is a functionally modified phosphono group and $X_2$ is a free or functionally modified phosphono group, converting $X_1$ and, where applicable, $X_2$ into the free phosphono group(s).

7 Claims, No Drawings

AZACYCLOALKYLALKANEDIPHOSPHONIC ACIDS USEFUL FOR TREATING DISEASES ATTRIBUTED TO CALCIUM METABOLISM DISORDERS

The invention relates to novel azacycloalkylalkanediphosphonic acids of formula

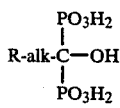

wherein R is an azabicycloalkyl radical that is attached by way of the aza ring member and is composed of ring systems each containing from 3 up to and including 8 members, and alk is lower alkylene, and their salts.

Azabicycloalkyl radicals that are attached by way of the aza ring member and are composed of ring systems each containing from 3 up to and including 8 members are composed especially of ring systems each containing from 4 to 8 members and are, for example, aza-$C_6$-$C_{10}$bicycloalkyl radicals that are attached by way of the aza ring member, such as 3-aza-bicyclo-$C_6$-$C_{10}$alk-3-yl radicals, and that are unsubstituted or substituted by up to and including 3 lower alkyl groups, e.g. 3-aza-bicyclo[3,1,0]hex-3-yl or 1,5-dimethyl-3-aza-bicyclo[3,1,0]hex-3-yl, 3-aza-bicyclo[3,2,0]hept-3-yl or 1,5-dimethyl-3-aza-bicyclo[3,2,0]hept-3-yl, 3-aza-bicyclo[3,1,1]hept-3-yl or 1,5-dimethyl-3-aza-bicyclo[3,1,1]hept-3-yl, 7-aza-bicyclo[2,2,1]hept-7-yl, 2-aza-bicyclo[3,2,1]oct-2-yl, 3-aza-bicyclo[3,2,1]oct-3-yl, 8-aza-bicyclo[3,2,1]oct-8-yl, 3-aza-bicyclo[3,2,2]non-3-yl or 3-aza-bicyclo[4,2,2]dec-3-yl.

The expression lower radicals and compounds is used hereafter to mean, for example, those radicals and compounds containing up to and including 7, especially up to and including 4, carbon atoms. The general definitions also have, for example, the following meanings:

Lower alkyl is, for example, $C_1$-$C_4$alkyl, such as methyl, ethyl, propyl, isopropyl, butyl, isobutyl, secondary butyl or tertiary butyl, but may also be a $C_5$-$C_7$alkyl group, that is to say a pentyl, hexyl or heptyl group.

Lower alkylene is, for example, $C_1$-$C_7$alkylene, especially $C_1$-$C_4$alkylene, preferably $C_2$-$C_4$alkylene, such as ethylene, 1,2- or 1,3-propylene, 1,2-, 1,3- or 1,4-butylene or 1,2-(2-methyl)propylene, but may also be 1,4- or 1,5-pentylene, 1,3-(3-methyl)butylene, 1,2-(2-ethyl)butylene or 1,4-(4-methyl)pentylene.

Salts of compounds of formula I are especially the salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, copper salts, aluminium salts or zinc salts, or ammonium salts with ammonia or organic amines or quaternary ammonium bases, such as optionally C-hydroxylated aliphatic amines, especially mono-, di- or tri-lower alkylamines, for example methyl-, ethyl-, dimethyl- or diethyl-amine, mono-, di- or tri-(hydroxy-lower alkyl)-amines, such as ethanol-, diethanol- or triethanol-amine, tris(hydroxymethyl)amino-methane or 2-hydroxy-tert.-butylamine, or N-(hydroxy-lower alkyl)-N,N-di-lower alkylamines or N-(polyhydroxy-lower alkyl)-N-lower alkylamines, such as 2-(dimethylamino)-ethanol or D-glucamine, or quaternary aliphatic ammonium hydroxides, for example tetrabutylammonium hydroxide.

The compounds of formula I and their salts have valuable pharmacological properties. In particular, they exhibit a pronounced regulatory action on the calcium metabolism of warm-blooded animals. In particular, in rats, they bring about pronounced inhibition of bone resorption, which can be demonstrated both in the test procedure according to Acta Endocrinol. 78, 613–24 (1975) by reference to the PTH-induced increase in the serum calcium level after subcutaneous administration in doses of from approximately 0.01 to approximately 1.0 mg/kg, and in the TPTX (thyroparathyroidectomised) rat model by reference to the experimental hypercalcaemia, induced by vitamin $D_3$, after the administration of doses of approximately from 0.001 to 1.0 mg s.c.. The tumour hypercalcaemia induced by Walker-256-tumours is likewise inhibited after peroral administration of from approximately 1.0 to approximately 100 mg/kg. Further, in adjuvant arthritis in rats in the test procedure according to Newbould, Brit. J. Pharmacology 21, 127 (1963) and according to Kaibara et al., J. Exp. Med. 159, 1388–96 (1984), they exhibit a marked inhibition of the progression of chronic arthritic processes in doses of approximately from 0.01 to 1.0 mg/kg s.c. They are therefore eminently suitable as active ingredients in medicaments for the treatment of diseases that can be attributed to calcium metabolism disorders, for example inflammatory processes in joints, degenerative processes in the articular cartilage, of osteoporosis, periodontitis, hyperparathyroidism and of calcium deposits in blood vessels or on prosthetic implants. A favourable effect is produced both in diseases in which an anomalous deposition of sparingly soluble calcium salts is to be observed, such as those from among the forms of arthritis, for example Bechterew's disease, neuritis, bursitis, periodontitis and tendinitis, fibrodysplasia, osteoarthrosis and of artereosclerosis, and in those diseases in which an anomalous degeneration of hard body tissue is the principal symptom, such as hereditary hypophosphatasia, degenerative processes in the articular cartilage, osteoporoses of various origins, Paget's disease and osteodystrophia fibrosa, and also in tumour-induced osteolytic processes.

The invention relates especially to compounds of formula I wherein R is an aza-bicyclo-$C_6$-$C_{10}$alkyl radical that is attached by way of the aza ring member and is composed of ring systems each containing from 3 up to and including 8, especially from 4 to 7, members, and alk is $C_1$-$C_7$alkylene, especially $C_1$-$C_4$alkylene, and their salts, especially their pharmaceutically acceptable salts with bases.

The invention relates more especially to compounds of formula I wherein R is an aza-bicyclo-$C_6$-$C_{10}$alkyl radical that is attached by way of the aza ring member and is composed of ring systems each containing from 4 to 7 members, such as 3-aza-bicyclo[3,1,0]hex-3-yl or 1,5-dimethyl-3-aza-bicyclo[3,1,0]hex-3-yl, 3-aza-bicyclo[3,2,0]hept-3-yl or 1,5-dimethyl-3-aza-bicyclo[3,2,0]hept-3-yl, 3-aza-bicyclo[3,1,1]hept-3-yl, 1,5-dimethyl-3-aza-bicyclo[3,1,1]hept-3-yl, 7-aza-bicyclo[2,2,1]hept-7-yl, 2-aza-bicyclo[3,2,1]oct-2-yl, 3-aza-bicyclo[3,2,1]oct-3-yl, 1,3,3-trimethyl-6-aza-bicyclo[3,2,1]oct-6-yl, 8-aza-bicyclo[3,2,1]oct-8-yl, 3-aza-bicyclo[3,2,2]non-3-yl or 3-aza-bicyclo[4,2,2]dec-3-yl, and alk is $C_2$-$C_7$alkylene, such as $C_2$-$C_4$alkylene, the free valencies of which extend from adjacent carbon atoms or from carbon atoms that are in the 1,3- or 1,4-position with respect to each other, and is, for example, ethylene, 1,3-propylene or 1,4-butylene, and their salts, especially their pharmaceutically acceptable salts with bases.

The invention relates most especially to compounds of formula I wherein R is a 3-aza-bicyclo[3,1,1]hept-3-yl radical, a 6-aza-bicyclo[3,2,1]oct-6-yl radical or a 3-aza-bicyclo[3,2,2]non-3-yl radical each of which is unsubstituted or substituted by up to and including three $C_1$–$C_4$alkyl, such as methyl, groups, for example 1,5-dimethyl-3-aza-bicyclo[3,1,1]hept-3-yl, 1,3,3-trimethyl-6-aza-bicyclo[3,2,1]oct-6-yl or 3-aza-bicyclo[3,2,2]non-3-yl, and alk is $C_2$–$C_4$alkylene of formula —$(CH_2)_n$— wherein n is 2, 3 or 4, especially ethylene, and their salts, especially their pharmaceutically acceptable salts with bases.

The invention relates first and foremost to compounds of formula I wherein R is 3-aza-bicyclo[3,1,1]hept-3-yl, 1,5-dimethyl-3-aza-bicyclo[3,1,1]hept-3-yl, 3-aza-bicyclo[3,2,1]oct-3-yl, 3-aza-bicyclo[3,2,2]non-3-yl or 3-azabicyclo[4,2,2]dec-3-yl, and alk is $C_2$–$C_4$alkylene of formula —$(CH_2)_n$— wherein n is 2, 3 or 4, and alk is accordingly, for example, ethylene, 1,3-propylene or 1,4-butylene, and their salts, especially their pharmaceutically acceptable salts with bases.

The invention relates specifically to the compounds of formula I mentioned in the Examples and to their salts, especially their internal salts and pharmaceutically acceptable salts with bases.

The invention also relates to a process for the preparation of compounds of formula I and their salts, which process is based on methods that are known per se. This process comprises (a) in a compound of formula

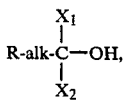
(II)

wherein $X_1$ is a functionally modified phosphono group X and $X_2$ is a free or functionally modified phosphono group X, converting the group(s) X into the free phosphono group(s), or (b) reacting a compound of formula R-alk-$X_3$,    (III)

wherein $X_3$ is carboxy, carbamoyl or cyano, with phosphorous acid and phosphorus trichloride, hydrolysing the primary product and, in an intermediate of formula

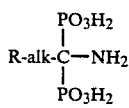
(IV)

obtained starting from compounds of formula III wherein $X_3$ is carbamoyl or cyano, or in a salt thereof, replacing the amino group by hydroxy by treatment with nitrous acid, and, if desired, converting a resulting compound into a different compound of formula I and/or converting a resulting free compound into a salt or converting a resulting salt into the free compound or into a different salt.

Functionally modified phosphono groups that are to be converted into free phosphono in accordance with process variant (a) are, for example, in the form of an ester, especially in the form of a diester of formula —P(=O)(OR$_1$)$_2$ (VII) wherein OR$_1$ is, in addition to lower alkoxy, a phenoxy group that is unsubstituted or substituted by lower alkyl, lower alkoxy, halogen, trifluoromethyl and/or by hydroxy.

The conversion of a functionally modified phosphono group into a free phosphono group is effected in customary manner by hydrolysis, for example in the presence of a mineral acid, such as hydrochloric or sulfuric acid, or by reaction with a tri-lower alkylhalosilane, for example trimethylchlorosilane or especially trimethylbromosilane, preferably while cooling, for example in a temperature range of from approximately 0° to approximately 25° C.

The starting materials of formula II can be prepared, for example, by reacting a compound of formula

R-alk-COOH,    (IIa)

or preferably the anhydride or acid chloride thereof, with a corresponding phosphorous acid triester of formula P(OR)$_3$ (IIb) in the presence of a tri-lower alkylamine, for example triethylamine, to form a compound of formula

(IIc)

and further reacting the latter with a phosphorous acid diester of formula H—P(=O)(OR)$_2$ or P(OH)(OR)$_2$ in the presence of a di-lower alkylamine, for example diethylamine, or in the presence of an alkali metal lower alkanolate, for example sodium methanolate, to form the corresponding compound of formula

(II')

Each of the above-mentioned reactions is advantageously carried out in the presence of a base.

Starting materials of formula IIa can, if they are not known, be prepared, for example, by reacting a corresponding compound of formula

Y-alk-COOR    (IId)

wherein Y is halogen, such as bromine, with an azabicycloalkane of formula R-H (IIf), or, for the preparation of compounds of formula IIa wherein alk is $C_2$–$C_7$alkylene the free valencies of which extend from adjacent carbon atoms, for example ethylene, reacting a compound of formula

alk'-COOR,    (IIe)

wherein alk' is a $C_2$–$C_7$alk-1-enyl radical, with an azabicycloalkane of formula R-H (IIf), and by hydrolysing the ester obtained in each case to the acid and anhydridising the latter, for example using phosphorus pentachloride.

Novel starting materials IIf can in their turn be prepared by reduction of corresponding (oxo or dioxo)azabicycloalkanes, especially those in which the oxo group(s) is(are) in the α-position with respect to the N-atom. An especially suitable reducing agent for this purpose is sodium dihydro-bis(2-methoxyethoxy)-aluminate. Thus, 3-aza-bicyclo[3,1,1]heptane, 1,5-dimethyl-3-aza-bicyclo[3,1,1]heptane, 3-aza-bicyclo[3,2,0]heptane and 1,5-dimethyl-3-aza-bicyclo[3,2,0]heptane are obtained in an elegant manner by treating 2,4-dioxo-3-aza-bicyclo[3,1,1]heptane, 1,5-dimethyl-2,4-dioxo-3-aza-bicyclo[3,1,1]heptane, 2,4-dioxo-3-aza-bicyclo[3,2,0]heptane and 1,5-dimethyl-2,4-dioxo-3-aza-bicyclo[3,2,0]heptane, respectively, with sodium dihydro-bis(2-methoxyethoxy)aluminate (approximately 70 % in toluene) at approximately from 20° to 40° C. in toluene as the solvent, and working up by hydrolysis in the presence of sodium hydroxide.

The reaction of compounds of formula III with phosphorous acid and phosphorus trichloride in accordance with process variant (b) is effected in customary manner, the phosphorous acid component preferably being formed in situ by reaction of excess phosphorus trichloride with water-containing phosphoric acid, for example with commercially available approximately 75% to 95%, preferably approximately 85%, phosphoric acid. The reaction is advantageously carried out while heating, for example at from approximately 70° to approximately 120° C., in a suitable solvent, such as tetrachloroethane, trichloroethane, chlorobenzene, chlorotoluene or paraffin oil, and with working up being effected by hydrolysis.

The treatment of intermediates of formula IV with nitrous acid is effected in customary manner with the latter being freed in aqueous solution from one of its salts, for example sodium nitrite, by acid treatment, for example by the action of hydrochloric acid, during which a corresponding, unstable diazonium salt, for example diazonium chloride, is formed as intermediate, which diazonium salt, with the introduction of the α-hydroxy group, splits off nitrogen.

The starting materials of formula III can, if they are not known, be prepared, for example, by reacting a corresponding compound of formula $$Y\text{-alk-COOR},\qquad\qquad\text{(IId)}$$

wherein Y is halogen, such as bromine, with an azabicycloalkane of formula R-H (IIf), or, for the preparation of compounds of formula III wherein alk is $C_2$–$C_7$alkylene the free valencies of which extend from adjacent carbon atoms, for example ethylene, by reacting a compound of formula $$\text{alk}'\text{-COOR},\qquad\qquad\text{(IIe)}$$

wherein alk' is a $C_2$–$C_7$alk-1-enyl radical, with an azabicycloalkane of formula R-H (IIf), and in each case hydrolysing the resulting ester to the acid.

Compounds of formula I obtained in accordance with the process of the invention or in accordance with another process that is known per se can be converted in a manner known per se into other compounds of formula I.

Depending on the starting materials and procedures chosen, the novel compounds may be in the form of one of the possible isomers or in the form of a mixture thereof, for example depending on the number of asymmetric carbon atoms, they may be in the form of pure optical isomers, such as antipodes, or in the form of isomeric mixtures, such as racemates, diastereoisomeric mixtures or mixtures of racemates.

Resulting diastereoisomeric mixtures and mixtures of racemates can be separated in known manner into the pure isomers, diastereoisomers or racemates on the basis of the physico-chemical differences between the components, for example by chromatography and/or fractional crystallisation.

Resulting racemates can also be resolved according to known methods into the optical antipodes, for example by recrystallisation from an optically active solvent, with the aid of microorganisms, or by reaction of an acid end product with an optically active base that forms salts with the racemic acid and by separation of the salts obtained in that manner, for example on the basis of their differing solubilities, into the diastereoisomers from which the antipodes can be freed by the action of suitable agents. Advantageously, the more active of the two antipodes is isolated.

Resulting free compounds of formula I can be converted into salts with bases by partial or complete neutralisation with one of the bases mentioned at the beginning.

Resulting salts can be converted into the free compounds in a manner known per se, for example by treatment with an acid reagent, such as a mineral acid, or, as the case may be, with a base, for example an alkali hydroxide.

The compounds, including their salts, may also be obtained in the form of their hydrates or may include the solvent used for crystallisation.

Owing to the close relationship between the novel compounds in free form and in the form of their salts, hereinbefore and hereinafter there is to be understood by the free compounds or their salts, where appropriate and expedient, optionally also the corresponding salts or free compounds, respectively.

The invention relates also to those embodiments of the process according to which a compound obtainable as an intermediate at any stage of the process is used as starting material and the remaining steps are carried out or a starting material is used in the form of a salt and/or racemate or antipode or especially is formed under the reaction conditions.

The starting materials that are used in the process of the present invention are preferably those which result in the compounds described at the beginning as being especially valuable. The invention relates also to novel starting materials and processes for the preparation thereof.

The pharmaceutical preparations according to the invention, which contain compounds of formula I or pharmaceutically acceptable salts thereof, are for enteral, such as oral or rectal, and parenteral administration and contain the pharmacological active ingredient on its own or together with a pharmaceutically acceptable carrier. The dosage of active ingredient depends on the species of warm-blooded animal, its age and individual condition and also on the mode of administration. The normal daily dosage to be recommended for a warm-blooded animal weighing approximately 75 kg is approximately from 30 to 1000 mg, preferably approximately from 100 to 1000 mg, in the case of oral administration, and approximately from 1 to 50 mg, preferably from 5 to 10 mg, in the case of intravenous administration, the dosage preferably being distributed between several equal partial doses.

The novel pharmaceutical preparations contain, for example, from approximately 10% to approximately 80%, preferably from approximately 20% to approximately 60%, active ingredient. Pharmaceutical preparations according to the invention for enteral and parenteral administration are, for example, those in dosage unit form, such as dragées, tablets, capsules or suppositories, and also ampoules. These are prepared in a manner known per se, for example by means of conventional mixing, granulating, confectioning, dissolving or lyophilising processes. For example, pharmaceutical preparations for oral administration can be obtained by combining the active ingredient with solid carriers, if desired granulating a resulting mixture and, if desired or necessary, processing the mixture or granulate, after the addition of suitable adjuncts, into tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatine, tragacanth, methylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating and lubricating agents, for example silica, talc, stearic acid or salts thereof, such as magnesium or calcium stearate, and/or polyethylene glycol. Dragée cores are provided with suitable coatings which may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules consisting of gelatine, and also soft sealed capsules consisting of gelatine and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, it being possible also to add stabilisers.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatine rectal capsules that contain a combination of the active ingredient with a base material; suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, or suspensions of the active ingredient, such as corresponding oily injection suspensions, in which suitable lipophilic solvents or vehicles, such as fatty oils, for example sesame oil, or synthetic fatty acid esters, for example ethyl oleate or triglycerides, are used, or aqueous injection suspensions that contain viscosity-increasing substances, for example sodium aarboxymethylcellulose, sorbitol and/or dextran and, if desired, also stabilisers.

The present invention relates also to the use of the compounds of formula I and their salts, preferably for the treatment of inflammation, especially for the treatment of inflammatory diseases of the rheumatic type, and more especially chronic arthritis, as well as for the treatment of diseases that are attributable to calcium metabolism disorders, for example of osteoporoses.

Dosages under 0.001 mg/kg of body weight have only a negligible effect on pathological calcification or the degeneration of hard tissue. At dosages above 100 mg/kg of body weight, toxic side-effects may occur in long-term use. The compounds of formula I and their salts can be administered both orally and, in the form of a hypertonic solution, subcutaneously, intramuscularly or intravenously. The preferred daily doses for these applications are in the range of approximately from 0.1 to 5 mg/kg in the case of oral administration, in the range of approximately from 0.1 to 1 mg/kg in the case of subcutaneous and intramuscular administration and in the range of approximately from 0.01 to 2 mg/kg in the case of intravenous administration.

The dosage of the compounds used is, however, variable and depends on the particular conditions, such as the nature and severity of the disease, duration of treatment and on the particular compound. Single doses contain, for example, from 0.01 to 10 mg, dosage unit forms for parenteral, such as intravenous, administration contain, for example, from 0.01 to 0.1 mg, preferably from 0.02 to 0.08 mg, and oral dosage unit forms contain, for example, from 0.2 to 2.5 mg, preferably from 0.3 to 1.5 mg, per kg of body weight. The preferred single dose for oral administration is from 10 to 100 mg and for intravenous administration from 0.5 to 5 mg. It is, however, possible to administer up to 4 single doses per day. The higher dosages in the case of oral administration are necessary owing to the limited absorption. In the case of long-term treatments, the initially higher dosage can normally be converted to low dosages while still maintaining the desired effect.

The following Examples illustrate the invention described above; they are not intended, however, to limit the scope thereof in any way. Temperatures are given in degrees Celsius.

EXAMPLE 1

11.68 g (0.05 mol) of 3-(1,5-dimethyl-3-aza-bicyclo[3,1,1]hept-3-yl)-propionic acid hydrochloride, 6.6 ml of 84% phosphoric acid and 23 ml of chlorobenzene are heated to 105° with stirring. 13.5 ml of phosphorus trichloride are slowly added dropwise and the reaction mixture is subsequently maintained at 105° for a further 3 hours. The chlorobenzene is then distilled off under reduced pressure, leaving a viscous mass. 50 ml of water are added to the latter and the mixture is boiled under reflux for 1 hour with stirring. The mixture is then completely concentrated by evaporation under reduced pressure. Upon stirring the residue with acetone and decanting, a colourless oil is obtained which is then dissolved in 50 ml of hot water. Upon adding 140 ml of hot methanol and cooling, colourless crystals of 3-(1,5-dimethyl-3-aza-bicyclo[3,1,1]hept-3-yl)-1-hydroxy-propane-1,1-diphosphonic acid are obtained; m.p. 245°–247° (decomposition); formula

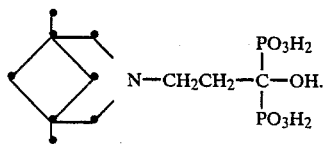

The 3-(1,5-dimethyl-3-aza-bicyclo[3,1,1]hept-3-yl)-propionic acid hydrochloride used as starting material can be prepared in the following manner:

A solution of 52.7 g of methacrylic acid chloride in 570 ml of methylene chloride is added dropwise to a stirred solution, cooled to from 0° to 5° C., of 71 g of N-tert.-butylmethacrylamide, 50.8 g of triethylamine and 570 ml of methylene chloride. Stirring is then carried out for 2½ hours and the reaction solution is left to stand for 4 days. After being concentrated, the reaction mixture is taken up in 0.5 liter of diethyl ether and filtered, and the solution is concentrated. The resulting red oil is filtered on silica gel with hexane/diethyl ether (4:1) yielding 3-(1,5-dimethyl-3-aza-bicyclo[3,1,1]hept-3-yl)-propionic acid hydrochloride in the form of a white crystalline product (m.p. 47°–48° C.).

A solution of 52.2 g of 2,6-dimethyl-4-tert.-butyl-p-cresol in 3.9 liters of methylene chloride is irradiated with ultraviolet light for 30 hours. After concentration, the crude product is chromatographed on 3 kg of silica gel 60 with toluene/diethyl ether (15:1) to yield the title compound in the form of white crystals having a melting point of 65°–65.5° C. (recrystallisation from n-pentane at −70° C.).

A solution of 47.6 g of 1,5-dimethyl-3-tert.-butyl-3-aza-bicyclo[3,1,1]heptane-2,4-dione in 215 ml of trifluoroacetic acid is heated under reflux for 6 hours. After concentration by evaporation, the reaction mixture is taken up in diethyl ether and the resulting crystalline product is filtered and washed with diethyl ether. The title compound of m.p. 195°–196° C. is thus obtained.

Under a nitrogen atmosphere, 80 ml of a solution of sodium dihydro-bis(2-methoxyethoxy)-aluminate in toluene (70%; FLUKA) are added dropwise to a stirred suspension of 1,5-dimethyl-3-aza-bicyclo[3,1,1]heptane-2,4-dione. During the addition, the temperature is kept in the range of from 25° to 35° C. by external cooling in an ice bath. When the addition is complete, the mixture is stirred for 15 minutes at room temperature and then heated under reflux for 1 hour. After cooling the mixture in an ice bath, 25.5 ml of concentrated sodium hydroxide solution are added dropwise to the mixture at from 10° to 15° C. The organic phase is decanted and the aqueous phase is washed with toluene. The combined organic phases are washed twice with 100 ml of water and once with 70 ml of brine. After the addition of magnesium sulfate, the organic phase is filtered and concentrated under a water-jet vacuum. The brownish oil is dissolved in 50 ml of absolute diethyl ether. By passing in HCl gas the title compound is obtained in the form of a crystalline product which, after being filtered with suction, is resuspended in diethyl ether and again filtered with suction and, finally, dried overnight under a high vacuum, to yield 1,5-dimethyl-3-aza-bicyclo[3,1,1]heptane hydrochloride in the form of colourless crystals of m.p. 144.5°–145.5°.

18.8 g of 1,1'-dimethyl-3-aza-bicyclo[3,1,1]heptane (0.15 mol) are introduced into 50 ml of diethyl ether, and 15.1 g of ethyl acrylate are gradually added thereto while stirring. A clear solution forms with a slight increase in temperature. After standing overnight at room temperature, the ether is distilled off. The oil which remains is the crude 3-(1,1'-dimethyl-3-aza-bicyclo[3,1,1]hept-3-yl)-propionic acid ethyl ester 32.06 g of 3-(1,1'-dimethyl-3-aza-bicyclo[3,1,1]hept-3-yl)-propionic acid ethyl ester are heated under reflux with 600 ml of 4N hydrochloric acid for 24 hours. The mixture is then completely concentrated by evaporation under reduced pressure and the crystalline residue is triturated with acetone. After filtering the crystals with suction, washing and drying, 3-(1,1'-dimethyl-3-aza-bicyclo[3,1,1]hept-3-yl)-propionic acid hydrochloride is obtained, m.p. 226°–228° C. (decomposition).

EXAMPLE 2

An aqueous solution of 5.15 g (15 mmol) of 3-(1,5-dimethyl-3-aza-bicyclo[3,1,1]hept-3-yl)-1-hydroxy-propane-1,1-diphosphonic acid and 7.26 g of tris(hydroxymethyl)-aminomethane is evaporated to dryness under reduced pressure. The residue is dissolved in methanol and then 2-propanol is added thereto, whereupon colourless crystals of di-[tris(hydroxymethyl)methyl]ammonium (1,5-dimethyl-3-aza-bicyclo[3,1,1]hept-3-yl)-1-hydroxy-propane 1,1-diphosphonate, i.e. the partial salt of 3-(1,5-dimethyl-3-aza-bicyclo[3,1,1]hept-3-yl)-1-hydroxy-propane-1,1-diphosphonic acid with 3-hydroxy-2,2-bis(hydroxymethyl)-1-aminopropane, separate out, m.p. 171°–174° (decomposition).

EXAMPLE 3

Analogously to Example 1, there is obtained from 3-aza-bicyclo[3,2,2]nonane via 3-(3-aza-bicyclo[3,2,2]-non-3-yl)-propionic acid hydrochloride, m.p. 227°–229°, 3-(3-aza-bicyclo[3,2,2]non-3-yl)-1-hydroxy-propane-1,1-diphosphonic acid, m.p. 145°–147°, of formula

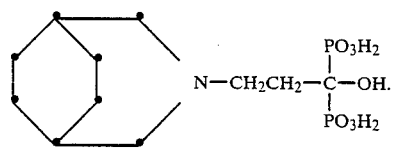

EXAMPLE 4

15.3 g of 1,3,3-trimethyl-6-aza-bicyclo[3,2,1]octane (0.15 mol) are introduced into 50 ml of diethyl ether, and 15.1 g of ethyl acrylate are gradually added thereto while stirring. A clear solution forms with a slight increase in temperature. After standing overnight at room temperature, the ether is distilled off. The oil which remains is distilled in vacuo to give 3-(1,3,3-trimethyl-6-aza-bicyclo[3,2,1]oct-6-yl)-propionic acid ethyl ester, b.p. 77°/0.013 mbar.

16.8 g of 3-(1,3,3-trimethyl-6-aza-bicyclo[3,2,1]oct-6-yl)-propionic acid ethyl ester (0.066 mol) are heated under reflux with 300 ml of 4N hydrochloric acid for 24 hours. The mixture is then completely concentrated by evaporation under reduced pressure and the crystalline residue is triturated with acetone. After filtering the crystals with suction, washing and drying, 3-(1,3,3-trimethyl-6-aza-bicyclo[3,2,1]oct-6-yl)-propionic acid hydrochloride, m.p. 183°–185° C. (decomposition) is obtained.

Analogously to Example 1, there is obtained from 3-(1,3,3-trimethyl-6-aza-bicyclo[3,2,1]oct-6-yl)-propionic acid hydrochloride 3-(1,3,3-trimethyl-6-aza-bicyclo[3,2,1]oct-6-yl)-1-hydroxypropane-1,1-diphosphonic acid, m.p. 195°–198° C. (decomposition), of formula

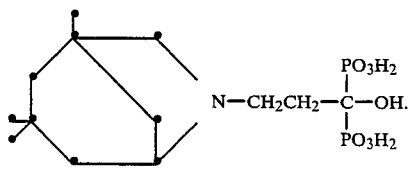

EXAMPLE 5

The following compounds may be prepared in a manner analogous to that described in Example 1:

3-(3-aza-bicyclo[3,1,0]hex-3-yl)-1-hydroxy-propane-1,1-diphosphonic acid;

2-(1,5-dimethyl-3-aza-bicyclo[3,1,0]hex-3-yl)-1-hydroxy-propane-1,1-diphosphonic acid;

3-(3-aza-bicyclo[3,2,0]hept-3-yl)-1-hydroxy-propane-1,1-diphosphonic acid;

3-(1,5-dimethyl-3-aza-bicyclo[3,2,0]hept-3-yl)-1-hydroxy-propane-1,1-diphosphonic acid;

3-(3-aza-bicyclo[3,1,1]hept-3-yl)-1-hydroxy-propane-1,1-diphosphonic acid;

3-(7-aza-bicyclo[2,2,1]hept-7-yl)-1-hydroxy-propane-1,1-diphosphonic acid;

3-(2-aza-bicyclo[3,2,1]oct-2-yl)-1-hydroxy-propane-1,1-diphosphonic acid;

3-(3-aza-bicyclo[3,2,1]oct-3-yl)-1-hydroxy-propane-1,1-diphosphonic acid;

3-(8-aza-bicyclo[3,2,1]oct-8-yl)-1-hydroxy-propane-1,1-diphosphonic acid and 3-(3-aza-bicyclo[4,2,2]dec-3-yl)-1-hydroxy-propane-1,1-diphosphonic acid, and the salts thereof, e.g. the disodium and tetrasodium salts thereof.

EXAMPLE 6

Tablets, each containing 25 mg of active ingredient, e.g. 3-(1,5-dimethyl-3-aza-bicyclo[3,1,1]hept-3-yl)-1-hydroxy-propane-1,1-diphosphonic acid or a salt thereof, e.g. the disodium salt thereof, can be prepared in the following manner:

| Constituents (for 1000 tablets) | |
|---|---|
| active ingredient | 25.0 g |
| lactose | 100.7 g |
| wheat starch | 7.5 g |
| polyethylene glycol 6000 | 5.0 g |
| talcum | 5.0 g |
| magnesium stearate | 1.8 g |
| demineralised water | q.s. |

Preparation

All the solid ingredients are first forced through a sieve of 0.6 mm mesh width. Then the active ingredient, the lactose, the talcum, the magnesium stearate and half of the starch are mixed. The other half of the starch is suspended in 40 ml of water and this suspension is added to a boiling solution of the polyethylene glycol in 100 ml of water, and the mixture is granulated, if necessary with the addition of water. The granulate is dried overnight at 35°, forced through a sieve of 1.2 mm mesh width and compressed to form tablets of approximately 6 mm diameter which are concave on both sides.

EXAMPLE 7

Tablets for chewing, each containing 30 mg of active ingredient, e.g. 3-(1,5-dimethyl-3-aza-bicyclo[3,1,1]hept-3-yl)-1-hydroxy-propane-1,1-diphosphonic acid or a salt thereof, e.g. the disodium salt thereof, can be prepared, for example, in the following manner:

| Composition: (for 1000 tablets) | |
|---|---|
| active ingredient | 30.0 g |
| mannitol | 267.0 g |
| lactose | 179.5 g |
| talcum | 20.0 g |
| glycine | 12.5 g |
| stearic acid | 10.0 g |
| saccharin | 1.0 g |
| 5% gelatine solution | q.s. |

Preparation

All the solid ingredients are first forced through a sieve of 0.25 mm mesh width. The mannitol and the lactose are mixed, and the mixture is granulated with the addition of gelatine solution and forced through a sieve of 2 mm mesh width, dried at 50° and again forced through a sieve of 1.7 mm mesh width. The active ingredient, the glycine and the saccharin are then carefully mixed, and the mannitol, the lactose granulate, the stearic acid and the talcum are added thereto, and the whole is thoroughly mixed and compressed to form tablets of approximately 10 mm diameter which are concave on both sides and have a breaking groove on the upper side.

EXAMPLE 8

Tablets, each containing 100 mg of active ingredient, e.g. 3-(1,5-dimethyl-3-aza-bicyclo[3,1,1]hept-3-yl)-1-hydroxy-propane-1,1-diphosphonic acid or a salt thereof, e.g. the disodium salt thereof, can be prepared in the following manner:

| Composition (for 1000 tablets) | |
|---|---|
| active ingredient | 100.0 g |
| lactose | 248.5 g |
| corn starch | 17.5 g |
| polyethylene glycol 6000 | 5.0 g |
| talcum | 15.0 g |
| magnesium stearate | 4.0 g |
| demineralised water | q.s. |

Preparation

The solid ingredients are first forced through a sieve of 0.6 mm mesh width. Then the active ingredient, the lactose, the talcum, the magnesium stearate and half of the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed to form tablets of approximately 10 mm diameter which are concave on both sides and have a breaking notch on the upper side.

EXAMPLE 9

In a manner analogous to that described in Examples 6 to 8, it is also possible to prepare pharmaceutical preparations containing another compound according to any one of Examples 1 to 5.

What is claimed is:

1. Azacycloalkylalkanediphosphonic acids of formula (I)

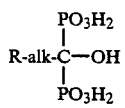

wherein R is a 3-azabicyclo[3.2.2]nonane radical which is unsubstituted by up to and including three $C_1$–$C_4$ alkyl groups and is attached by way of the aza ring member and alk is lower alkylene and pharmaceutically acceptable salts thereof.

2. A compound according to claim 1 being 3-(3-Azabicyclo[3,2,2]non-3-yl)-1-hydroxy-propane-1,1-diphosphonic acid or a pharamaceutically acceptable salt thereof.

3. Azacycloalkylalkanediphosphonic acids according to claim 1 wherein alk is $C_1$–$C_7$ alkylene and pharmaceutically acceptable salts thereof.

4. Azacyclo alkylalkanephosphonic acids according to claim 1 wherein alk is $C_2$–$C_7$ alkylene the free valancies of which extend from adjacent carbon atoms or from carbon atoms that are in the 1,3- or 1,4-position with respect to each other and pharmaceutically acceptable salts thereof.

5. Azacycloalkylalkanediphosphonic acids according to claim 1 wherein alk is $C_2$–$C_4$ alkylene of formula —$(CH_2)_n$— wherein n is 2,3 or 4 and pharmaceutically acceptable salts thereof.

6. A pharmaceutical composition consisting essentially of an effective amount of a compound according to claim 1 together with conventional pharmaceutical adjuncts.

7. A method of treating diseases in which an anomalous deposition of sparingly soluble calcium salts or an anomalous degeneration of hard body tissues is the principal symptom which comprises administering an effective amount of a compound according to claim 1 or a pharmaceutically acceptable salt thereof to a warm-blooded animal in need thereof.

* * * * *